United States Patent [19]

Maffrand et al.

[11] 4,424,356

[45] Jan. 3, 1984

[54] PROCESS FOR THE PREPARATION OF 5,6,7,7A-TETRAHYDRO-4H-THIENO-[3,2,-C]PYRIDIN-2-ONE

[75] Inventors: Jean-Pierre Maffrand, Portet-sur-Garonne, France; Norio Suzuki, Chiba, Japan; Kynichi Matsubayashi, Funabashi, Japan; Shinichiro Ashida, Ichikawa, Japan

[73] Assignee: Sanofi, Paris, France

[21] Appl. No.: 325,795

[22] Filed: Nov. 30, 1981

[30] Foreign Application Priority Data

Nov. 28, 1980 [FR] France ................................ 80 25275

[51] Int. Cl.³ .......................................... C07D 495/04
[52] U.S. Cl. ................................................. 546/114
[58] Field of Search ..................... 546/114; 549/52, 62

[56] References Cited

FOREIGN PATENT DOCUMENTS 2345150 10/1977 France .

*Primary Examiner*—Henry R. Jiles
*Assistant Examiner*—Bernard Dentz
*Attorney, Agent, or Firm*—Weiser & Stapler

[57] ABSTRACT

The present invention provides a process for the preparation of 5,6,7,7a-tetrahydro-4H-pyridin-2-one derivatives of the general formula:

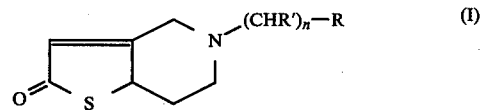

in which R is a hydrogen atom or a phenyl radical optionally substituted by at least one halogen atom, lower alkyl radical, lower alkoxy radical, nitro group, carboxy group, alkoxycarbonyl radical or cyano group; R' is a hydrogen atom or a lower alkyl radical and n is 0, 1, 2, 3 or 4; and of their addition salts with mineral or organic acids, wherein a compound of the general formula:

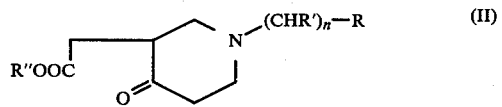

in which R, R' and n have the same meanings as above and R'' is a hydrogen atom or an alkyl radical containing up to 4 carbon atoms, is treated in an organic solvent with gaseous hydrogen choloride and gaseous hydrogen sulphide. The compounds have platelet anti-aggregant and anti-thrombotic properties.

8 Claims, No Drawings

PROCESS FOR THE PREPARATION OF 5,6,7,7A-TETRAHYDRO-4H-THIENO-[3,2,-C]PYRIDIN-2-ONE

The present invention is concerned with a novel process for the preparation of 5,6,7,7a-tetrahydro-4H-thieno(3,2-c)pyridin-2-one derivatives.

The 5,6,7,7a-tetrahydro-4H-thieno(3,2-c)pyridin-2-one derivatives with which the present invention is concerned are compounds of the general formula:

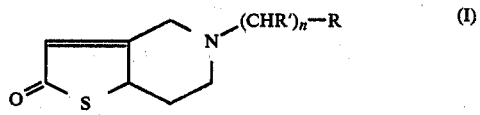

in which R is a hydrogen atom or a phenyl radical optionally substituted by at least one halogen atom, lower alkyl radical, lower alkoxy radical, nitro group, carboxy group, alkoxycarbonyl radical or cyano group; R' is a hydrogen atom or a lower alkyl radical and n is 0, 1, 2, 3 or 4; as well as the addition salts thereof with mineral and organic acids.

These compounds (I) have platelet anti-aggregant properties and anti-thrombotic properties and are the subject matter of another Patent Application which we have filed simultaneously.

They are also included in a general formula given in French Patent Specification Nos. 73 03 503 and 75 24 486 in the following tautomeric form:

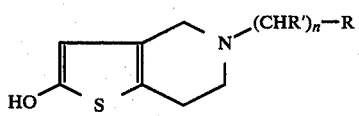

in which R, R' and n have the same meanings as above.

However, none of the compounds (I) is specifically described therein.

According to the present invention, there is provided a process for the preparation of compounds of general formula (I), wherein a compound of the general formula:

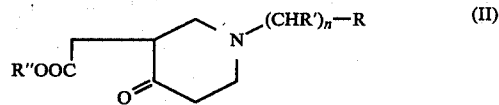

in which R, R' and n have the same meanings as above and R" is a hydrogen atom or an alkyl radical containing up to 4 carbon atoms, is treated in an organic solvent with gaseous hydrogen chloride and gaseous hydrogen sulphide.

The action of the gaseous hydrogen chloride and of the gaseous hydrogen sulphide may be carried out simultaneously with a mixture of the two gases or by the separate and successive action of each of them.

The reaction is carried out in an organic solvent, for example a lower alkanol, such as methanol or ethanol, or a lower carboxylic acid, such as acetic acid or propionic acid, or in a mixture of these solvents.

The reaction may be carried out at a temperature of from ambient temperature to the boiling temperature of the solvent used.

The keto acids and keto esters of general formula (II) may be prepared by a process analogous to that described in published Japanese Patent Application Kokai No. 79 98 771 in the name of Tokyo Koho, which is referred to in Chemical Abstracts, 92, 41773x/1980, for the preparation of compounds of general formula (II) in which R' is a hydrogen atom, R is a phenyl radical and n is 1 or 2.

The following Examples are given for the purpose of illustrating the present invention, the structure of the compounds obtained being confirmed by microanalysis, infra-red spectroscopy and nuclear magnetic resonance.

EXAMPLE 1

5-(2-Chlorobenzyl)-5,6,7,7a-tetrahydro-4H-thieno(3,2-c)-pyridin-2-one. (Formula I; R=2—Cl.C$_6$H$_4$; r'=H; n=1).

(a) Preparation of methyl [1-(2-chlorobenzyl)-4-oxopiperid-3-yl]-acetate.

A solution of 100 g. (0.355 mole) ethyl [1-(2-chlorobenzyl)-4-oxopiperid-3-yl]-carboxylate (see J. P. Maffrand and D. Frehel, Bull. Soc. Chim. France, (1-2), II-48/1978) in 400 cc. 1,2-dimethoxyethane is added dropwise to a mixture of 17.04 g. (0.355 mole) sodium hydride (50% suspension) in 250 cc. 1,2-dimethoxyethane. The reaction mixture is stirred at ambient temperature for 30 minutes, after which a solution of 59.28 g. (0.355 mole) ethyl bromoacetate in 250 cc. 1,2-dimethoxyethane is added thereto dropwise.

The reaction mixture is stirred at ambient temperature for 2 hours and the precipitate formed is filtered off and washed with diethyl ether and the filtrate is concentrated in a vacuum. The evaporation residue is taken up in water and extracted with methylene chloride. The organic extracts are washed with water, dried over anhydrous sodium sulphate and filtered through a bed of silica and the filtrate is concentrated in a vacuum.

The yellow resin obtained (123.2 g.) is dissolved in 850 cc. 6 N hydrochloric acid and the solution is boiled under reflux, under an atmosphere of nitrogen, for 4 hours. After cooling, the reaction mixture is concentrated in a vacuum and water is added, followed by extraction with diethyl ether. The aqueous phases are rendered weakly basic by the addition of sodium carbonate, then adjusted to a pH of about 4 by the addition of acetic acid and extracted with methylene chloride. The organic phases are washed with water, dried with anhydrous sodium sulphate and evaporated to dryness. The resinous product obtained (93.8 g.) is dissolved in acetone and treated with an ethereal solution of gaseous hydrogen chloride. The [1-(2-chlorobenzyl)-4-oxopiperid-3-yl]-acetic acid hydrochloride obtained is filtered off, washed with acetone and then with diethyl ether and dried in a vacuum. This compound is obtained in a yield of 64% in the form of white crystals; m.p. decomposes at about 180° C.; IR (KBr): $\nu CO = 1728$ cm$^{-1}$.

A solution of 30 g. of this hydrochloride in 300 cc. methanol saturated with gaseous hydrogen chloride is stirred at ambient temperature for 3 hours. The reaction mixture is then evaporated in a vacuum at a temperature below 50° C. and the residue is poured into water, rendered basic by the addition of sodium bicarbonate and extracted with methylene chloride. The organic extracts are washed with water, dried with anhydrous sodium sulphate and evaporated to dryness. The yellow resin obtained is used, without further purification, for the following stage.

IR (film): $\nu CO = 1720$ cm$^{-1}$; NMR (CDCl$_3$) = 7.05–7.65 (m,4H); 3.72 (s,2H); 3.62 (s,3H).

(b)

5-(2-Chlorobenzyl)-5,6,7,7a-tetrahydro-4H-thieno(3,2-c)-pyridin-2-one.

Currents of gaseous hydrogen chloride and of gaseous hydrogen sulphide are bubbled into a solution, heated to 85° C., of 4.5 g. (0.0152 mole) of the keto ester obtained above in (a) in 45 cc. acetic acid. The reaction mixture is then concentrated in a vacuum and the residue is taken up in water, adjusted to a basic pH by the addition of sodium bicarbonate and extracted with methylene chloride. The extracts are washed with water, dried with anhydrous sodium sulphate and evaporated to dryness. The yellow oil obtained (3.6 g.; yield 86% of theory) is converted into the oxalate by the addition of a solution of oxalic acid in acetone; m.p. 170° C., after recrystallisation from ethanol; IR (KBr): $\nu CO = 1660$ cm$^{-1}$ (large).

The corresponding hydrochloride hemihydrate, after precipitation from acetone, decomposes at about 180° C.

The corresponding free base, after recrystallisation from ethanol, melts at 73°–74.5° C. NMR (CDCl$_3$) = 7.1–7.6 (m,4H); 6.2 (s,1H); 4.2–4.7 (m,1H); 3.9 (s,2H); 1.5–4.2 (m,6H).

EXAMPLES 2 TO 9

The following compounds were prepared in the same manner as described above in Example 1:

Derivative 2: 5-Benzyl-5,6,7,7a-tetrahydro-4H-thieno(3,2-c)-pyridin-2-one
formula (I) (R=C$_6$H$_5$; R'=H; n=1)
maleate: beige crystals; m.p. 132°–134° C. (recrystallised from isopropanol)
IR (KBr): $\nu CO$: 1680 cm$^{-1}$
base: NMR (CDCl$_3$): 7.25 (m,5H); 5.90 (s,1H); 3.60 (s,2H).

Derivative 3: 5-(4-chlorobenzyl)-5,6,7,7a-tetrahydro-4H-thieno-(3,2-c)-pyridin-2-one
formula (I) (R=4—Ch—C$_6$H$_4$; R'=H; n=1)
maleate: beige crystals; m.p. 158°–160° C. (recrystallised from ethanol)
IR (KBr): $\nu CO = 1680$ cm$^{-1}$
base: NMR (CDCl$_3$): 7.30 (m,4H); 6.0 (s,1H); 3.50 (s,2H).

Derivative 4: 5-(2-methylbenzyl)-5,6,7,7a-tetrahydro-4H-thieno-(3,2-c)-pyridin-2-one
formula (I) (R=2—CH$_3$—C$_6$H$_4$; R'=H; n=1)
oxalate: beige crystals; m.p. 195°–197° C. (recrystallised from methanol)
IR (KBr): $\nu CO = 1690$ cm$^{-1}$
base: NMR (CDCl$_3$): 7.10 (s,4H); 5.90 (s,1H); 3.55 (s,2H); 2.30 (s,3H).

Derivative 5: 5-[1-(2-chlorophenyl)-ethyl]-5,6,7,7a-tetrahydro-4H-thieno-(3,2-c)-pyridin-2-one
formula (I) (R=2—Cl—C$_6$H$_4$; R'=CH$_3$; n=1)
hydrochloride: yellow crystals; m.p. 140°–142° C.
IR (KBr): $\nu CO = 1690$ cm$^{-1}$
base: NMR (CDCl$_3$): 7.30 (m, 4H); 6.05; 5.95 (2s,1H); (2 diastereoisomers).

Derivative 6: 5-[1-(2-chlorophenyl)-propyl]-5,6,7,7a-tetrahydro-4H-thieno(3,2-c)-pyridin-2-one
formula (I) (R=2—Cl—C$_6$H$_4$; R'=C$_2$H$_5$; n=1)
hydrochloride: beige crystals; m.p. 124°–126° C.
IR (KBr): $\nu CO = 1690$ cm$^{-1}$
base: NMR (CDCl$_3$): 7.30 (m,4H); 6.05; 5.90 (2s,1H) (2 diastereoisomers).

Derivative 7: 5-(2-cyanobenzyl)-5,6,7,7a-tetrahydro-4H-thieno(3,2-c)-pyridin-2-one
formula (I) (R=2—Cl—C$_6$H$_4$; R'=H; n=1)
oxalate: beige crystals; m.p. 176°–178° C. (recrystallised from acetonitrile)
IR (KBr): $\nu CO = 1700$ cm$^{-1}$; $\nu CN = 2210$ cm$^{-1}$
base: NMR (CDCl$_3$): 7.50 (m,4H); 6.00 (s,1H); 3.80 (s,2H).

Derivative 8: 5-(2-nitrobenzyl)-5,6,7,7a-tetrahydro-4H-thieno(3,2-c)-pyridin-2-one
formula (I) (R=2—NO$_2$—C$_6$H$_4$; R'=H; n=1)
oxalate: beige crystals; m.p. 186°–188° C. (recrystallised from isopropanol-ethanol)
IR: $\nu CO = 1685$ cm$^{-1}$
base: NMR (CDCl$_3$): 7.50 (m,4H); 5.95 (s,1H); 3.90 (s,2H).

Derivative 9: 5-(2-bromobenzyl)-5,6,7,7a-tetrahydro-4H-thieno(3,2-c)-pyridin-2-one
formula (I) (R=2—Br—C$_6$H$_4$; R'=H; n=1)
oxalate: beige crystals; m.p. 151°–153° C. (recrystallised from isopropanol)
IR (KBr): $\nu CO = 1690$ cm$^{-1}$
base: (CDCl$_3$): 7.30 (m,4H); 5.95 (s,1H); 3.75 (s,2H).

We claim:

1. Process for the preparation of 5,6,7,7a-tetrahydro-4H-pyridin-2-one derivatives of the formula:

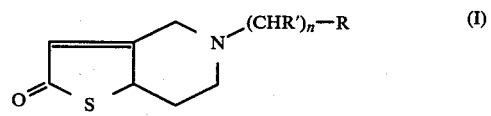

in which R is hydrogen or phenyl substituted by at least one halogen, lower alkyl, lower alkoxy, nitro, carboxy, alkoxycarbonyl or cyano; R' is hydrogen or a lower alkyl and n is 0, 1, 2, 3 or 4; and of their addition salts with mineral or organic acids, wherein a compound of the formula:

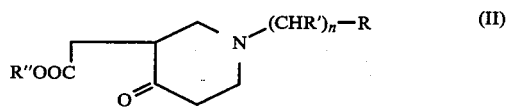

in which R, R' and n have the same meanings as above and R" is hydrogen or alkyl containing up to 4 carbon atoms, is treated in an organic solvent with gaseous hydrogen chloride and gaseous hydrogen sulphide.

2. Process according to claim 1, wherein the gaseous hydrogen chloride and the gaseous hydrogen sulphide are used in the form of a mixture.

3. Process according to claim 1, wherein the gaseous hydrogen chloride and the gaseous hydrogen sulphide are used separately and successively.

4. Process according to claim 1, wherein the organic solvent used is a lower alkanol or a lower carboxylic acid or a mixture thereof.

5. Process according to claim 4, wherein the lower alkanol used is methanol or ethanol.

6. Process according to claim 4, wherein the lower carboxylic acid used is acetic acid or propionic acid.

7. Process according to claim 5, wherein the lower carboxylic acid used is acetic acid or propionic acid.

8. Process according to claim 1, 2, 3, 4, 5 or 6 wherein the treatment with gaseous hydrogen chloride and gaseous hydrogen sulphide is carried out at a temperature of from ambient temperature to the boiling point of the solvent.

* * * * *